(12) United States Patent
Exner et al.

(10) Patent No.: US 11,741,988 B2
(45) Date of Patent: Aug. 29, 2023

(54) ELECTRONIC DEVICE AND METHOD FOR CONTACT TRACING

(71) Applicant: Sony Group Corporation, Tokyo (JP)

(72) Inventors: Peter Exner, Malmö (SE); Hannes Bergkvist, Helsingborg (SE)

(73) Assignee: SONY GROUP CORPORATION, Tokyo (JP)

( * ) Notice: Subject to any disclaimer, the term of this patent is extended or adjusted under 35 U.S.C. 154(b) by 34 days.

(21) Appl. No.: 17/531,740

(22) Filed: Nov. 20, 2021

(65) Prior Publication Data

US 2022/0199109 A1 Jun. 23, 2022

(30) Foreign Application Priority Data

Dec. 21, 2020 (SE) .................. 2051511-0

(51) Int. Cl.
*G10L 25/78* (2013.01)
*G10L 25/51* (2013.01)

(52) U.S. Cl.
CPC .............. *G10L 25/78* (2013.01); *G10L 25/51* (2013.01); *G10L 2025/783* (2013.01)

(58) Field of Classification Search
CPC ... G10L 25/78; G10L 25/51; G10L 2025/783; G16H 40/67; G16H 50/80; A61B 5/0823; A61B 5/6898; H04W 4/023; H04W 4/80
See application file for complete search history.

(56) References Cited

U.S. PATENT DOCUMENTS

| | | | |
|---|---|---|---|
| 9,344,811 B2 * | 5/2016 | Bakish | ................... A41D 13/11 |
| 10,430,896 B2 | 10/2019 | Horie | |
| 10,667,057 B1 | 5/2020 | Adams | |
| 11,026,177 B1 * | 6/2021 | Chung | ............... H04W 52/0277 |
| 11,504,011 B1 * | 11/2022 | Jain | ........................ A61B 5/1118 |
| 2013/0179285 A1 * | 7/2013 | Lyle | ........................ G06Q 30/06 |
| | | | 705/26.1 |
| 2013/0318027 A1 | 11/2013 | Almogy | |

(Continued)

FOREIGN PATENT DOCUMENTS

CN 111342916 A 6/2020

OTHER PUBLICATIONS

Office Action and Search Report from corresponding Swedish Application No. 2051511-0, dated Sep. 3, 2021, 8 pages.

(Continued)

*Primary Examiner* — Fariba Sirjani

(74) *Attorney, Agent, or Firm* — TUCKER ELLIS LLP

(57) ABSTRACT

A first electronic device includes an interface; microphone circuitry; memory circuitry; and processor circuitry. The first electronic device is configured to discover, via the interface, a first wireless network. The first electronic device is configured to receive, via the interface, from a second electronic device discovering the first wireless network, a voice biometric indicative of a second user. The first electronic device is configured to activate the microphone circuitry to detect an input audio signal. The first electronic device is configured to determine whether the detected input audio signal satisfies one or more criteria. The first electronic device is configured to, when the detected input audio signal satisfies the one or more criteria, determine a parameter indicative of a level of risk of exposure; and generate, based on the parameter, contact data.

20 Claims, 4 Drawing Sheets

(56) References Cited

U.S. PATENT DOCUMENTS

| | | | |
|---|---|---|---|
| 2017/0209102 A1* | 7/2017 | Parthasarathy | A61B 5/0059 |
| 2018/0040076 A1* | 2/2018 | Horie | G06F 3/0481 |
| 2018/0041591 A1* | 2/2018 | Yoden | H04L 12/2814 |
| 2018/0053176 A1* | 2/2018 | Rawat | G06Q 20/3278 |
| 2018/0290020 A1 | 10/2018 | Vissa et al. | |
| 2019/0252078 A1 | 8/2019 | Schubert | |
| 2019/0282160 A1* | 9/2019 | Gilmartin | A61B 5/742 |
| 2020/0258535 A1 | 8/2020 | Vatanparvar | |
| 2020/0342083 A1* | 10/2020 | Goldstein | H04W 4/21 |
| 2022/0130415 A1* | 4/2022 | Garrison | G10L 25/51 |
| 2022/0369048 A1* | 11/2022 | McKinney | H04R 25/50 |

OTHER PUBLICATIONS

Cong T. Nguyen et al.: "Enabling and Emerging Technologies for Social Distancing: A Comprehensive Survey and Open Problems"; School of Electrical and Data Engineering; dated Sep. 22, 2020; 43 pages.

* cited by examiner

ELECTRONIC DEVICE AND METHOD FOR CONTACT TRACING

RELATED APPLICATION DATA

This application claims the benefit of Swedish Application No. 2051511-0, filed Dec. 21, 2020, the disclosure of which is incorporated herein by reference in its entirety.

TECHNICAL FIELD

The present disclosure relates to electronic devices and methods for contact tracing.

BACKGROUND

An approach to handling disease outbreaks is to perform contact tracing. Each time an infection is identified in a person, there is an attempt to identify other persons who may have been in the proximity of the infected person while the person was infectious.

For example, a public health official contacts the person with a verified infection and inquires about places visited and the persons that have been met. However, sharing personal information is often met with privacy concerns.

Contact tracing can be performed by registering the Service Set Identifier(s), SSID(s) collected by the mobile phones equipped with, for example Bluetooth or WiFi, and registering nearby SSIDs as possible contacts.

However, such contact tracing based solely on Bluetooth or WiFi does not necessarily imply risk of exposure.

SUMMARY

Therefore, such contact tracing based solely on Bluetooth or WiFi is seen as noisy, generates many false positives and renders contact tracing hard to manage.

Accordingly, there is a need for electronic devices and methods for contact tracing, which mitigate, alleviate or address the shortcomings existing and provide an improved precision and robustness of data for contact tracing while maintaining privacy.

A first electronic device is disclosed. The first electronic device is configured to be operated by a first user. The first electronic device comprises an interface; microphone circuitry; memory circuitry; and processor circuitry. The first electronic device is configured to discover, via the interface, a first wireless network. The first electronic device is configured to receive, via the interface, from a second electronic device discovering the first wireless network, a voice biometric indicative of a second user. The first electronic device is configured to activate the microphone circuitry to detect an input audio signal. The first electronic device is configured to determine whether the detected input audio signal satisfies one or more criteria. The first electronic device is configured to, when the detected input audio signal satisfies the one or more criteria, determine a parameter indicative of a level of risk of exposure; and generate, based on the parameter, contact data.

Disclosed is a method, performed by a first electronic device, for contact tracing. The first electronic device comprises an interface; microphone circuitry; memory circuitry; and processor circuitry. The method comprises discovering, via the interface, a first wireless network. The method comprises receiving, via the interface, from a second electronic device discovering the first wireless network, a voice biometric indicative of a second user. The method comprises activating the microphone circuitry to detect an input audio signal. The method comprises determining whether the detected input audio signal satisfies at least one of one or more criteria. The method comprises determining a parameter indicative of a level of risk of exposure, when the detected input audio signal satisfies the at least one of the one or more criteria. The method comprises generating contact data based on the parameter when the detected input audio signal satisfies the at least one of the one or more criteria.

It is an advantage of the present disclosure that precision and robustness of contact data for contact tracing is improved without violating privacy of a user. Advantageously, the disclosed method and disclosed first electronic device lead to a reduced number of false positive contact cases. Advantageously, the disclosed method and disclosed first electronic device preserve privacy at least in that the disclosed technique does not require that private conversations are recorded. The disclosed method and disclosed first electronic device enables anonymous exchange of voice biometrics.

BRIEF DESCRIPTION OF THE DRAWINGS

The above and other features and advantages of the present disclosure will become readily apparent to those skilled in the art by the following detailed description of examples thereof with reference to the attached drawings, in which.

DETAILED DESCRIPTION

Figure 1:
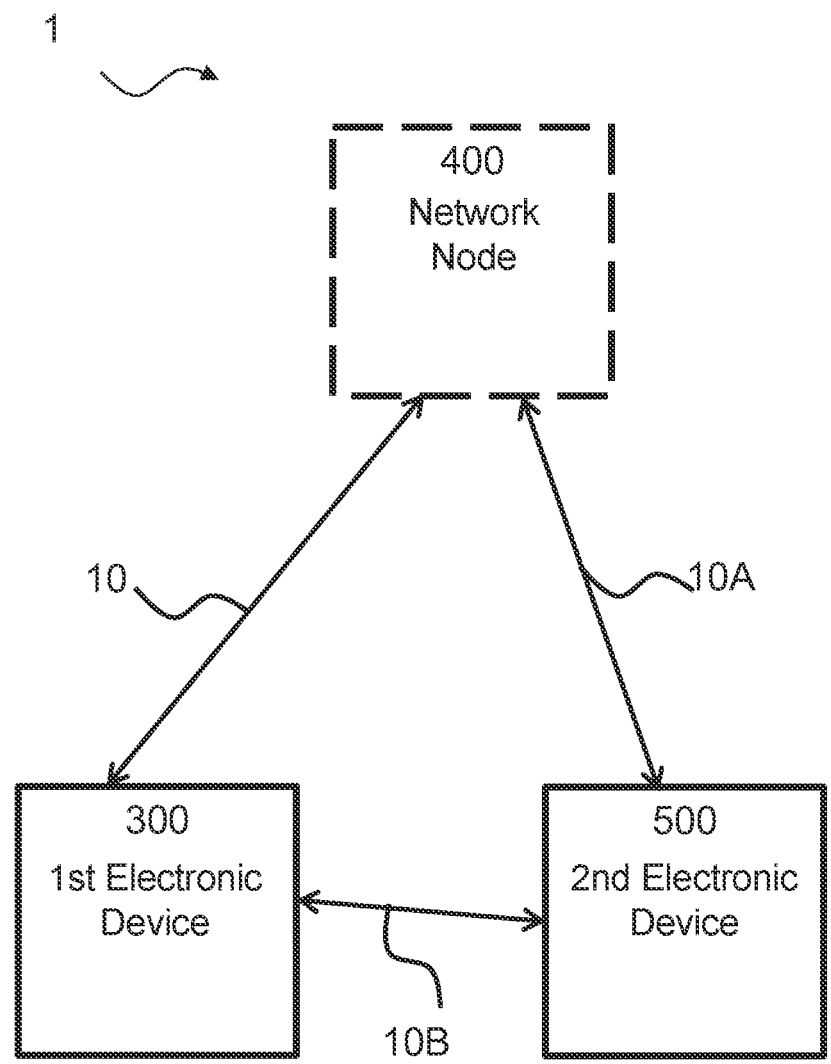
FIG. 1 is a diagram illustrating an example first wireless network comprising an example first electronic device and an example second electronic device according to this disclosure.

Various examples and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the examples. They are not intended as an exhaustive description of the disclosure or as a limitation on the scope of the disclosure. In addition, an illustrated example needs not have all the aspects or advantages shown. An aspect or an advantage described in conjunction with a particular example is not necessarily limited to that example and can be practiced in any other examples even if not so illustrated, or if not so explicitly described.

The figures are schematic and simplified for clarity, and they merely show details which aid understanding the disclosure, while other details have been left out. Throughout, the same reference numerals are used for identical or corresponding parts.

FIG. 1 is a diagram illustrating an example first wireless network 1 comprising an example first electronic device 300, an example second electronic device 500 and optionally an example network node 400 according to this disclosure.

As discussed in detail herein, the present disclosure relates to a first wireless network 1. For example, the first wireless network 1 comprises a short-range wireless communication network, such as a Wireless Local Area Network, WLAN (such as IEEE 802.11, and/or Wireless Fidelity, WiFi) and/or a Bluetooth network. The first wireless network 1 comprises an example first electronic device 300, an example second electronic device 500.

An electronic device (such as the first electronic device and/or the second electronic device) may refer to a wireless device, such as a mobile device and/or a user equipment, UE.

The first electronic device 300 may be configured to communicate with the second electronic device 500 via wireless link 10B and optionally with the network node 400 via a wireless link (or radio link) 10.

The second electronic device 500 may be configured to communicate with the first electronic device 300 via wireless link 10B and optionally with the network node 400 via a wireless link (or radio link) 10A.

A network node disclosed herein refers to an access network node, such as an access point operating in short-range wireless system, which may be fixed or mobile (such as a mobile hot-spot). In one or more examples, the network node is a functional unit which may be distributed in several physical units.

The first wireless network 1 described herein may comprise a plurality of electronic devices 300, 500, and/or one or more network nodes 400, such as one or more access points.

The present disclosure relates to contact tracing, so that for example, each time an infection is identified in a person, there is an attempt to identify other persons (people) who may have been in the proximity while the person was infectious. However, such contact tracing based solely on Bluetooth or WiFi does not necessarily imply risk of exposure. Therefore, such contact tracing based solely on Bluetooth or WiFi is seen as noisy, generating many false positives and renders contact tracing hard to manage.

In an example scenario where the disclosed technique is applied, two or more users may have engaged in a conversation and may be likely to have been in close proximity of each other. It may be appreciated that the disclosed technique may be seen as filtering possible contact or contact cases based on voice biometrics from one or more electronic devices (or other microphone enabled devices). When a first wireless network 1 is discovered by a first electronic device 300 of a first user (such as via a broadcasted connection identifier) and optionally added to the list, the first electronic device 300 receives a voice biometric indicative of a second user from the second electronic device of the second user which discovers the first wireless network 1. When a first wireless network 1 is discovered by a first electronic device 300 of a first user (such as via a broadcasted connection identifier), the first electronic device 300 turns on the microphone circuitry of the first electronic device to capture and/or detect and/or record an input audio signal which may indicate the voice biometric indicative of the second user. Optionally, the first electronic device 300 may perform face mask detection on the input audio signal to detect a face mask (such as a surgical mask) or face shield. Optionally, the first electronic device 300 may detect cough or sneezing (this may impact the one or more criteria). The first electronic device 300 is configured to determine whether the detected input audio signal satisfies one or more criteria (such as, related to duration, voice level, and/or matching between the detected audio input signal and the received voice biometric). Based on the satisfaction of the one or more criteria, a close proximity can be assessed by the first electronic device configured to determine a parameter indicative of a level of risk of exposure and generate, based on the parameter, contact data.

The first electronic device 300 may be configured to identify the second electronic device 500 by a connection identifier of the second electronic device 500, such as a device identifier of the second electronic device.

A connection identifier disclosed herein may be seen as an identifier identifying a connection for the first electronic device, such as a device identifier of another device in connection with the first electronic device, and/or a network identifier of a wireless network that the first electronic device has discovered.

A device identifier may be seen as an identifier uniquely identifying an electronic device, such as a universally unique identifier. A network identifier may be seen as an identifier uniquely identifying a network, such as an Service Set Identifier, SSID. A service set may be seen as a group of devices which are identified by the same SSID.

The first electronic device 300 may be configured to identify the network node 400 by a connection identifier of the wireless network of the network node 400, such as a network identifier.

The first electronic device 300 may be configured to maintain a list of nearby connection identifiers, such a least of nearby SSI Ds and/or device identifiers, optionally continuously. The nearby networks may include a second wireless network and/or a third wireless network, each having a network identifier different from network identifier of the first wireless network 1.

Figure 2:
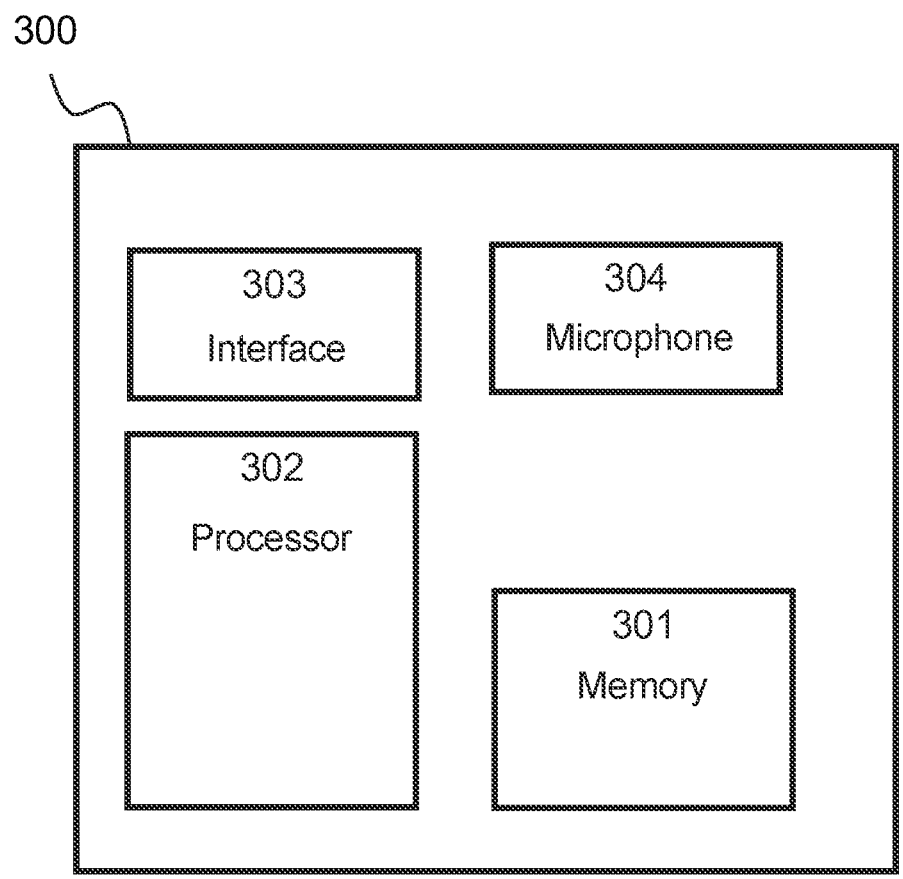
FIG. 2 is a block diagram illustrating an example first electronic device according to this disclosure.

FIG. 2 shows a block diagram of an example first electronic device 300 according to the disclosure. The first electronic device 300 comprises memory circuitry 301, processor circuitry 302, an interface 303 and microphone circuitry 304. The first electronic device 300 may be configured to perform any of the methods disclosed in FIGS. 3A-3B. In other words, the first electronic device 300 may be configured for contact tracing.

The first electronic device 300 is configured to communicate, for example by using the interface 303, with a second electronic network node, such as the second electronic network node disclosed herein, optionally by using a first wireless network.

The interface 303 may be seen as a wireless interface configured for wireless communications via a first wireless network, such as a short-range wireless network, such as WiFi and/or Bluetooth.

The first electronic device 300 is optionally configured to be operated by a first user. The first electronic device 300 may be seen as a user electronic device, such as an electronic device that is configured to be operated by a user. In some examples, the electronic device may comprise a face shield, for example, connectable to the face shield. For example, a face shield may be configured to act as the first electronic device, in that the face shield may have the first electronic device integrated. A face shield may be seen as an item of personal protective equipment that aims to protecting a part of the face. A face shield may comprise one or more of: a mask (such as a surgical mask and/or a face mask) and/or a visor.

The first electronic device 300 is configured to discover, via the interface 303, a first wireless network such as a short range wireless network. For example, the first electronic device 300 is configured to discover, via the interface 303, a first wireless network such as first wireless network 1 of FIG. 1, such as a short-range wireless network, such as a Bluetooth network, such as a WiFi network. For example, first electronic device 300 is configured to discover, via the interface 303, a second electronic device, such as second electronic device 500 of FIG. 1, wherein the first electronic device and the second electronic device form the first wireless network.

The first electronic device 300 is configured to receive, via the interface 303, from a second electronic device (such as second electronic device 500 of FIG. 1), a voice biometric indicative of a second user. A voice biometric disclosed here may be seen as uniquely identifying characteristics of an individual's voice, such as a voice fingerprint of an individual. For example, a voice biometric disclosed herein may comprise a voice fingerprint. For example, a voice biometric may be used to identify an individual and/or may be used to match or associate an audio signal to an individual. The second electronic device is optionally configured to be operated by the second user. For example, the second electronic device may be discovering the first wireless network which is also discovered by the first electronic device. In some example, in response to the first wireless network being discovered by the first electronic device and the second electronic device, the voice biometric indicative of the second user is received by the first electronic device. It may be appreciated that in the present disclosure, a voice biometric is transmitted to the first electronic device (and optionally vice versa) only when the first wireless network is discovered (such as when a Bluetooth connection has been discovered or established to the second electronic device), and thereby only when needed.

In one or more examples, the first electronic device 300 is configured to receive an encrypted voice biometric indicative of the second user, which was encrypted by the second electronic device by applying homomorphic encryption. Homomorphic encryption allows the first electronic device to perform calculations on encrypted voice biometric indicative of the second user without decrypting it first.

The first electronic device 300 is configured to activate the microphone circuitry 304 to detect an input audio signal. In other words, the microphone circuitry 304 is only turned briefly on when the first wireless network is discovered (such as when a Bluetooth connection has been discovered or established to the second electronic device). This may lead to some power savings.

The first electronic device 300 is configured to determine whether the detected input audio signal satisfies one or more criteria. For example, one or more criteria comprises a first criterion, and/or a second criterion, and/or a third criterion. In other words, the first electronic device 300 is configured to determine whether the detected input audio signal satisfies at least one of the one or more criteria, for example to determine whether the detected input audio signal satisfies the first criterion, and/or the second criterion and/or the third criterion.

The first electronic device 300 is configured to determine a parameter indicative of a level of risk of exposure when the detected input audio signal satisfies the one or more criteria. A parameter indicative of a level of risk of exposure disclosed herein may be seen as a parameter that provides a level of risk of exposure, such as risk of exposure to a disease and/or an affliction, such as a contagious disease that may be propagated by close proximity or contact. In other words, the parameter may indicate the level of possible exposure of the first user to the risk of a contagious disease that may be propagated by close proximity or contact. For example, the parameter may be based on the level of proximity between two users, such as level of close proximity. For example, the level of risk of exposure may comprise a lower level, a medium level, and/or a higher level. For example, the level of risk of exposure may be a gradual level. For example, the first electronic device 300 is configured to determine the parameter indicative of the level of risk of exposure when the detected input audio signal satisfies at least one criterion, such as the first criterion, and/or the second criterion and/or the third criterion. The parameter may indicate a level of a contact or a level of close proximity, for example between the first user and the second user. The parameter may indicate a level of interaction, for example between the first user and the second user. A contact may be seen as a proximity level that does not require physical contact, but that is still sufficient for contagion.

The first electronic device 300 is configured to generate, based on the parameter, contact data. The contact data may be seen as data indicative of a contact, such as level of risk of exposure that is deemed by the first electronic device 300 as sufficient to correspond to a contact. For example, the contact data may indicate information regarding parties that may be considered to have been in close proximity for contagion. In one or more example first electronic devices, the contact data is indicative of a first user identifier of the first user associated with a second user identifier of the second user. A user identifier (such as the first user identifier and/or the second user identifier) may be seen as an identifier uniquely identifying the user while not disclosing a user identity, such as an anonymous identifier (such as the anonymous first user identifier and/or the anonymous second user identifier). For example, the user identifier (such as the first user identifier and/or the second user identifier) may be provided during an initialization phase, such as when onboarding (such as registering) the user to a contact tracing application and/or a contact tracing platform and/or a contact tracing system. In some examples, a user identifier may be based on a device identifier. For example, a device identifier may serve as a user identifier. In one or more example first electronic devices, the first user identifier is randomized (such as pseudo-randomized). In one or more example first electronic devices, the second user identifier is randomized (such as pseudo-randomized). In one or more example first electronic devices, the first user identifier is anonymized; and/or wherein the second user identifier is anonymized.

In one or more example first electronic devices, the contact data is indicative of a first connection identifier of the first wireless network, such as a network identifier of the first wireless network, such an SSID.

In one or more example first electronic devices, the determination of whether the detected input audio signal satisfies the at least one of the one or more criteria comprises a comparison of the detected input audio signal with the received voice biometric. For example, the detected input audio signal comprises an extracted voice biometric associated with the second user, such as by using Natural Language NL entity recognition to extract a name, such as a nickname. The first electronic device 300 may be configured to compare the extracted voice biometric with the received voice biometric.

In one or more example first electronic devices, the one or more criteria comprises a first criterion based on a first threshold and on the comparison. For example, the first criterion is satisfied when the detected input audio signal matches the received voice biometric at least by or above the first threshold. For example, the first threshold may be indicative of a tolerance margin or a tolerance threshold (for example, 90%). In other words, the first criterion helps assess that the detected input audio signal matches at least 90% of the received voice biometric. For example, the one or criteria comprises a first criterion based on the comparison, and wherein the first criterion is satisfied when the detected input audio signal matches the received second voice biometric at least in part.

In one or more examples, the first electronic device 300 is configured to deactivate the microphone circuitry for detection of the input audio signal, for example when the audio input signal is determined to satisfy the one or more criteria, such as the first criterion. In one or more examples, the first electronic device 300 is configured to deactivate the microphone circuitry for detection of the input audio signal, for example when it is determined that the first electronic device is not in the range of the first wireless network, is unable to discover the first wireless network any longer, such as due to a disconnection event.

In one or more example first electronic devices, the one or more criteria comprises a second criterion based on a second threshold. The second threshold may be indicative of a voice level, such as an amplitude of the voice. The second criterion may be satisfied when a voice level of the detected input audio signal is above the second threshold. For example, the voice level of the detected input audio signal is above the second threshold, indicating a certain proximity. For example, the voice level of the detected input audio signal is above a pre-given threshold, indicating a certain proximity.

In one or more example first electronic devices, the one or more criteria comprises a third criterion based on a third threshold. For example, the third threshold may be indicative of duration of contact. The duration of contact may be seen as duration of the risk of exposure, such as exposure time. For example, the third criterion is satisfied when a duration of contact is above the third threshold. For example, the duration of contact, for example while located in the vicinity of the first wireless network, is above the third threshold, which is selected, such as by a learning model, based on the level of risk of exposure and a given contagious disease. In one or more example first electronic devices, the contact data comprises the duration of contact. The duration of contact may be determined by the first electronic device 300 based on a duration during which the first electronic device 300 detects the first wireless network and/or the second electronic device.

In one or more example first electronic devices, the duration of contact is determined based on the detected input audio signal and a range. The range may be seen as the range of the first wireless network based on the wireless technology used, such as Bluetooth and/or WiFi. The range may be seen as a distance, for example expressed in meters.

In one or more example first electronic devices, the first electronic device 300 is configured to detect based on the detected input audio signal that a face shield is worn by the second user. For example, a learning model may be trained on voice utterances with and without a mask across a range of users. In some example, detecting the presence of a face shield, such as a mask may lead to a parameter indicative of a higher level of risk of exposure, because the face shield or mask is worn by a user who is ill, which is usual in some regions of the world. In some examples, detecting the presence of a face shield, such as a mask may lead to a parameter indicative of lower level of risk of exposure because the face shield or mask is worn by a user who is healthy and wants to avoid catching a disease, which is usual in some regions of the world. In one or more example first electronic devices, the contact data comprises a face shield parameter indicating presence of the face shield.

In some examples, the contact data may comprise a value indicating if the name or nickname of the first user has been detected or extracted in a voice utterance of the second user. This indicates for example when the second user greeted the first user with the first user's name and/or nickname. In some examples, the first electronic device and the second electronic device may exchange each other's names and/or nicknames.

In one or more example first electronic devices, the first electronic device 300 is configured to detect, based on the detected input audio signal, a coughing (such as of the second user) and/or a sneezing (such as of the second user). For example, the first electronic device 300 may comprise a detector configured to detect coughing and/or sneezing based on the input audio signal, such as to distinguish coughing and/or sneezing from other sounds and also possibly identify the affliction or disease. For example, the first electronic device 300 may be configured to associate, based on additional discourse analysis, the detected coughing and/or sneezing to the utterance of a user.

In one or more example first electronic devices, the first electronic device 300 is configured to determine an estimate of risk of exposure based on a learning model for risk of exposure and the contact data. The learning model may be seen as a scheme that characterizes the risk of exposure based on the contact data, such as including the first threshold, the second threshold, and/or the third threshold, and/or a face shield parameter and/or if a coughing and/or sneezing was detected. Example of learning models may comprise random forest including for example: a register, a combination of the contact data with test results (such as positive or negative), and correlating the results and exposure time, and adjusting one or more thresholds. The random forest is seen as a classification algorithm consisting of many decision trees. In other words, a learning model can be trained in the cloud to adjust thresholds (such as the first threshold, the second threshold, and/or the third threshold) when an affliction has been registered for a pair of users. This may lead to an adaption to exposure that depends on for example personal protection worn by users, contact time, and proximity to others.

In one or more example first electronic devices, the first electronic device 300 is configured to adjust the one or more criteria based on the learning model. For example, the first electronic device may use the learning model to update and/or adjust one or more of the first threshold, the second threshold, and the third threshold.

In one or more example first electronic devices, the first electronic device 30 is configured to train the learning model based on the contact data, for example for future estimates. Alternatively, or additionally, the first electronic device 30 is configured to train the learning model based on previous contact, for determining the estimate of risk of exposure. For example, the learning model is trained based on the contact data associated with negative/positive cases from for example public health authorities. Input data to the training includes a pair of randomized user identifiers, duration of contact, if a personalized greeting was detected, and/or whether either users wore face shields. In some example, the first electronic device 30 is configured to train the learning model based on the contact data training by requesting a server device to train the learning model.

In one or more example first electronic devices, the first electronic device 300 is configured to transmit the contact data to an external device, such as to a server device, such as to a cloud service, such as to a contact tracing system. In one or more example first electronic devices, the first electronic device 300 is configured to receive, from an external device, such as a server device, one or more of: an exposure estimate, and a set of thresholds including the first threshold and/or the second threshold and/or the third threshold.

In one or more example first electronic devices, the first electronic device 300 is configured to notify the first user based on the contact data, such as via a contact tracing application, such as by displaying, on a display of the first electronic device, a user interface object representative of a notification of a potential contamination, such a preliminary exposure level and warning. In one or more example first electronic devices, the first electronic device 300 is configured to notify the first user by a server device, a cloud.

In one or more example first electronic devices, the first electronic device 300 is configured to generate a list of connection identifiers comprising a first connection identifier associated with the first wireless network.

In one or more example first electronic devices, the first electronic device 300 is configured to transmit, via the interface, to the second electronic device, a voice biometric indicative of the first user. In other words, the voice biometric indicative of the first user may be denoted as a first voice biometric while the voice biometric of the second user may be denoted as a second voice biometric. To preserve privacy, the first electronic device 300 may be configured to encrypt the voice biometric indicative of the first user, by applying homomorphic encryption, and to transmit the encrypted voice biometric to the second electronic device. Homomorphic encryption allows the second electronic device to perform calculations on encrypted voice biometric indicative of the first user without decrypting it first.

In one or more example first electronic devices, the first electronic device 300 is configured to activate the microphone circuitry to continuously detect an input audio signal. This may lead to increasing the likelihood of the true positive contact tracing.

In one or more example first electronic devices, the voice biometric indicative of the second user is text independent or text dependent. A text dependent fingerprint may additionally be an utterance containing the user's name or nickname. The user's name or nickname may be seen as a text extractable from the utterance. A text may be seen as a word spoken by a user. This can for example be extracted from recorded audio input signal through use of Natural Language Processing NLP algorithms, such as entity recognition. A text independent biometric may for example be composed of spectral features of a recorded voice utterance made by the user beforehand.

In one or more example first electronic devices, the voice biometric of the first user is text independent or text dependent.

The first electronic device 300 may be configured to delete from the memory circuitry 301 voice biometric indicative of the second user, once the contact data is generated or the parameter indicative of the level of risk of exposure is determined.

Figure 3A:
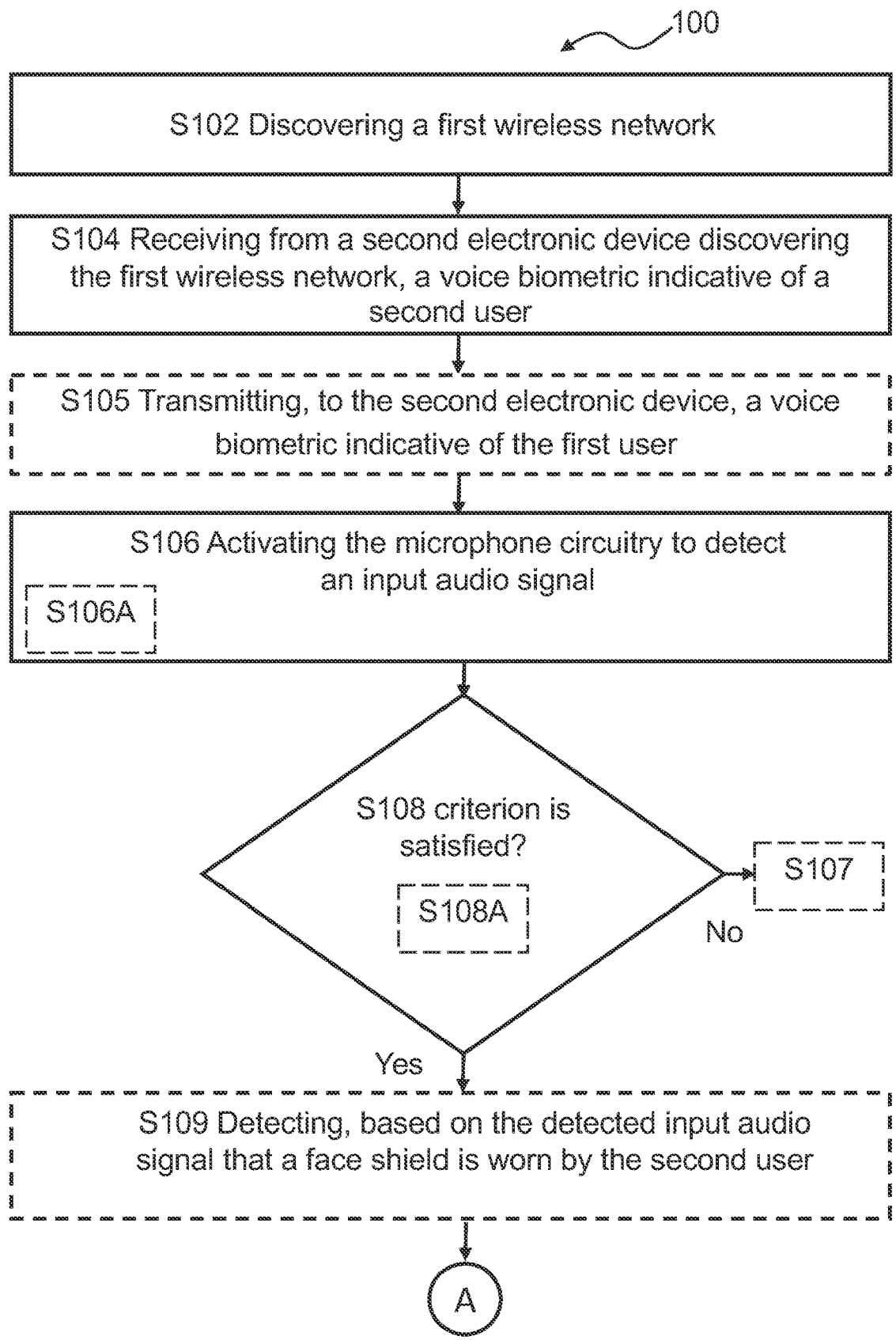
FIGS. 3A-3B are flow-charts illustrating an example method, performed by a first electronic device, for contract tracing according to this disclosure.
Figure 3B:
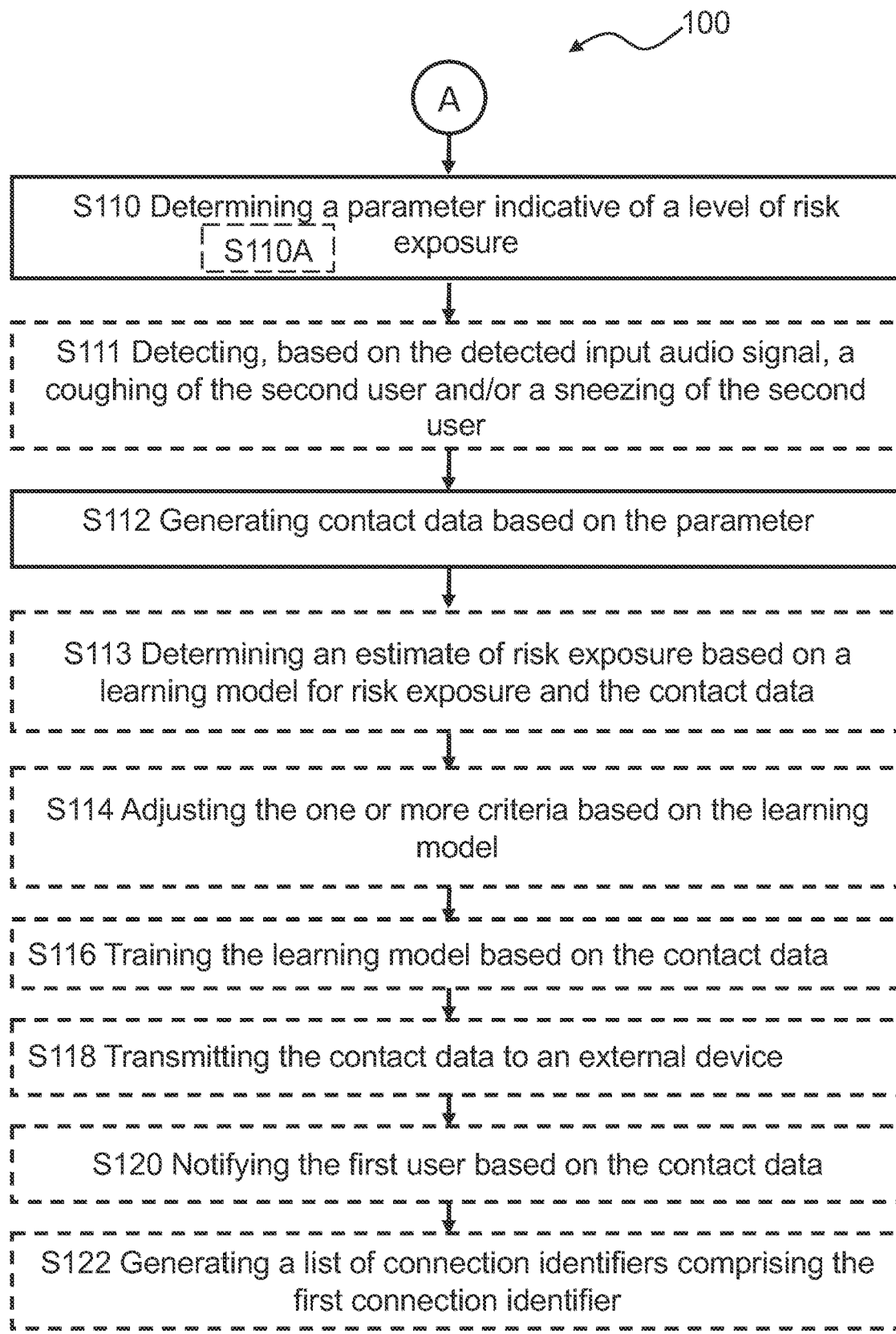

The first electronic device 300 is optionally configured to perform any of the operations disclosed in FIGS. 3A-3B (such as any one or more of S105, S106A, S108A, S107, S109, S110, S110A, S111, S113, S114, S116, S118, S120, S122). The operations of the first electronic device 300 may be embodied in the form of executable logic routines (for example, lines of code, software programs, etc.) that are stored on a non-transitory computer readable medium (for example, memory circuitry 301) and are executed by processor circuitry 302).

Furthermore, the operations of the first electronic device 300 may be considered a method that the first electronic device 300 is configured to carry out. Also, while the described functions and operations may be implemented in software, such functionality may also be carried out via dedicated hardware or firmware, or some combination of hardware, firmware and/or software.

Memory circuitry 301 may be one or more of a buffer, a flash memory, a hard drive, a removable media, a volatile memory, a non-volatile memory, a random access memory (RAM), or other suitable device. In a typical arrangement, memory circuitry 301 may include a non-volatile memory for long term data storage and a volatile memory that functions as system memory for processor circuitry 302. Memory circuitry 301 may exchange data with processor circuitry 302 over a data bus. Control lines and an address bus between memory circuitry 301 and processor circuitry 302 also may be present (not shown in FIG. 2). Memory circuitry 301 is considered a non-transitory computer readable medium.

Memory circuitry 301 may be configured to store data (such as voice biometric of the first user) in a part of the memory.

FIGS. 3A-3B are flow-charts illustrating an example method 100, performed by a first electronic device, for contact tracing according to the disclosure. The first electronic device (such as the first electronic device disclosed herein, such as electronic device 300 of FIG. 1) comprises an interface; microphone circuitry; memory circuitry; and processor circuitry.

The method 100 comprises discovering S102, via the interface, a first wireless network. The method 100 comprises receiving S104, via the interface, from a second electronic device discovering the first wireless network, a voice biometric indicative of a second user. In one or more example methods, the second electronic device is configured to be operated by the second user. The method 100 comprises activating S106 the microphone circuitry to detect an input audio signal. The method 100 comprises determining S108 whether the detected input audio signal satisfies at least one of one or more criteria. The method 100 comprises determining S110 a parameter indicative of a level of risk of exposure, when the detected input audio signal satisfies the at least one of the one or more criteria. The method 100 comprises generating S112 contact data based on the parameter.

In one or more example methods, the method 100 comprises forgoing S107 the determination of the parameter indicative of the level of risk of exposure, and the generation of the contact data when the detected input audio signal does not satisfy the one or more criteria.

In one or more example methods, determining S108 whether the detected input audio signal satisfies the at least one of the one or more criteria comprises comparing S108A the detected input audio signal with the second voice biometric.

In one or more example methods, the determining S110 comprises determining S110A the parameter indicative of the level of risk of exposure based on the learning model and optionally previous contact data (such as contact data generated earlier) and/or contact data from others.

In one or more example methods, the detected input audio signal comprises an extracted voice biometric associated with the second user.

In one or more example methods, the one or more criteria comprises a first criterion based on a first threshold and on the comparison.

In one or more example methods, the first criterion is satisfied when the detected input audio signal matches the received voice biometric at least by or above the first threshold.

In one or more example methods, the one or more criteria comprises a second criterion based on a second threshold.

In one or more example methods, the second criterion is satisfied when a voice level of the detected input audio signal is above the second threshold.

In one or more example methods, the one or more criteria comprises a third criterion based on a third threshold.

In one or more example methods, the third criterion is satisfied when a duration of contact is above the third threshold.

In one or more example methods, the duration of contact is determined based on the detected input audio signal and a range.

In one or more example methods, the contact data is indicative of a first user identifier of the first user associated with a second user identifier of the second user.

In one or more example methods, the first user identifier is randomized. In one or more example methods, the second user identifier is randomized.

In one or more example methods, the contact data is indicative of a first connection identifier associated with the first wireless network.

In one or more example methods, the method 100 comprises detecting S109 based on the detected input audio signal that a face shield is worn by the second user.

In one or more example methods, the contact data comprises a face shield parameter indicating presence of the face shield.

In one or more example methods, the method 100 comprises detecting S111, based on the detected input audio signal, a coughing of the second user and/or a sneezing of the second user.

In one or more example methods, the method 100 comprises determining S113 an estimate of risk of exposure based on a learning model for risk of exposure and the contact data.

In one or more example methods, the method 100 comprises adjusting S114 the one or more criteria based on the learning model.

In one or more example methods, the method 100 comprises training S116 the learning model based on the contact data.

In one or more example methods, the method 100 comprises transmitting S118 the contact data to an external device.

In one or more example methods, the method 100 comprises notifying S120 the first user based on the contact data.

In one or more example methods, the method 100 comprises generating S122 a list of connection identifiers comprising a first connection identifier.

In one or more example methods, the method 100 comprises transmitting S105, via the interface, to the second electronic device, a voice biometric indicative of the first user.

In one or more example methods, the activating S106 comprises activating S106A the microphone circuitry to continuously detect an input audio signal.

In one or more example methods, the method 100 comprises deactivating the microphone circuitry for detection of the input audio signal, when the audio input signal is determined to satisfy the one or more criteria (such as the first criterion).

Examples of methods and products (first electronic devices) according to the disclosure are set out in the following items:

Item 1. A first electronic device, wherein the first electronic device is configured to be operated by a first user, the first electronic device comprising:
an interface;
microphone circuitry;
memory circuitry; and
processor circuitry;
wherein the first electronic device is configured to:
discover, via the interface, a first wireless network;
receive, via the interface, from a second electronic device discovering the first wireless network, a voice biometric indicative of a second user, wherein the second electronic device is configured to be operated by the second user;
activate the microphone circuitry to detect an input audio signal;
determine whether the detected input audio signal satisfies one or more criteria,
when the detected input audio signal satisfies the one or more criteria:
determine a parameter indicative of a level of risk of exposure; and
generate, based on the parameter, contact data.

Item 2. The first electronic device according to item 1, wherein the determination of whether the detected input audio signal satisfies the at least one of the one or more criteria comprises a comparison of the detected input audio signal with the received voice biometric.

Item 3. The first electronic device according to any of the previous items, wherein the detected input audio signal comprises an extracted voice biometric associated with the second user.

Item 4. The first electronic device according to any of items 2-3, wherein the one or more criteria comprises a first criterion based on a first threshold and on the comparison, and wherein the first criterion is satisfied when the detected input audio signal matches the received voice biometric at least by or above the first threshold.

Item 5. The first electronic device according to any of the previous items, wherein the one or more criteria comprises a second criterion based on a second threshold; wherein the second criterion is satisfied when a voice level of the detected input audio signal is above the second threshold.

Item 6. The first electronic device according to any of the previous items, wherein the one or more criteria comprises a third criterion based on a third threshold; wherein the third criterion is satisfied when a duration of contact is above the third threshold.

Item 7. The first electronic device according to item 6, wherein the duration of contact is determined based on the detected input audio signal and a range.

Item 8. The first electronic device according to any of the previous items, wherein the contact data is indicative of a first user identifier of the first user associated with a second user identifier of the second user.

Item 9. The first electronic device according to item 8, wherein the first user identifier is randomized; and/or wherein the second user identifier is randomized.

Item 10. The first electronic device according to any of the previous items, wherein the contact data is indicative of a first connection identifier of the first wireless network.

Item 11. The first electronic device according to any of the previous items, wherein the first electronic device is configured to detect based on the detected input audio signal that a face shield is worn by the second user.

Item 12. The first electronic device according to any of the previous items, wherein the contact data comprises a face shield parameter indicating presence of the face shield.

Item 13. The first electronic device according to any of the previous items, wherein the first electronic device is configured to detect, based on the detected input audio signal, a coughing and/or a sneezing.

Item 14. The first electronic device according to any of the previous items, wherein the first electronic device is configured to determine an estimate of risk of exposure based on a learning model for risk of exposure and the contact data.

Item 15. The first electronic device according to the item 14, wherein the first electronic device is configured to adjust the one or more criteria based on the learning model.

Item 16. The first electronic device according to the any of items 14-15, wherein the first electronic device is configured to train the learning model based on the contact data.

Item 17. The first electronic device according to any of the previous items, wherein the first electronic device is configured to transmit the contact data to an external device.

Item 18. The first electronic device according to any of the previous items, wherein the first electronic device is configured to notify the first user based on the contact data.

Item 19. The first electronic device according to any of the previous items, wherein the first electronic device is configured to generate a list of connection identifiers comprising a first connection identifier associated with the first wireless network.

Item 20. The first electronic device according to any of the previous items, wherein the first electronic device is configured to transmit, via the interface, to the second electronic device, a voice biometric indicative of the first user.

Item 21. The first electronic device according to any of the previous items, wherein the first electronic device is configured to activate the microphone circuitry to continuously detect an input audio signal.

Item 22. The first electronic device according to any of the previous items, wherein the voice biometric is text independent or text dependent.

Item 23. The first electronic device according to any of the previous items, wherein the first electronic device is configured to deactivate the microphone circuitry for detection of the input audio signal, when the audio input signal is determined to satisfy the one or more criteria.

Item 24. A method, performed by a first electronic device, for contact tracing, wherein the first electronic device comprises an interface; microphone circuitry; memory circuitry; and processor circuitry; the method comprising:
 discovering (S102), via the interface, a first wireless network;
 receiving (S104), via the interface, from a second electronic device discovering the first wireless network, a voice biometric indicative of a second user, wherein the second electronic device is configured to be operated by the second user;
 activating (S106) the microphone circuitry to detect an input audio signal;
 determining (S108) whether the detected input audio signal satisfies at least one of one or more criteria, when the detected input audio signal satisfies the at least one of the one or more criteria:
  determining (S110) a parameter indicative of a level of risk of exposure; and
  generating (S112) contact data based on the parameter.

Item 25. The method according to item 24, wherein determining (S108) whether the detected input audio signal satisfies the at least one of the one or more criteria comprises comparing (S108A) the detected input audio signal with the received voice biometric.

Item 26. The method according to any of items 24-25, wherein the detected input audio signal comprises an extracted voice biometric associated with the second user.

Item 27. The method according to any of items 24-26, wherein the one or more criteria comprises a first criterion based on a first threshold and on the comparison, and wherein the first criterion is satisfied when the detected input audio signal matches the received voice biometric at least by or above the first threshold.

Item 28. The method according to any of items 24-27, wherein the one or more criteria comprises a second criterion based on a second threshold; wherein the second criterion is satisfied when a voice level of the detected input audio signal is above the second threshold.

Item 29. The method according to any of items 24-28, wherein the one or more criteria comprises a third criterion based on a third threshold; wherein the third criterion is satisfied when a duration of contact is above the third threshold.

Item 30. The method according to item 29, wherein the duration of contact is determined based on the detected input audio signal and a range.

Item 31. The method according to any of items 24-30, wherein the contact data is indicative of a first user identifier of the first user associated with a second user identifier of the second user.

Item 32. The method according to item 31, wherein the first user identifier is randomized; and/or wherein the second user identifier is randomized.

Item 33. The method according to any of items 24-32, wherein the contact data is indicative of a first connection identifier associated with the first wireless network.

Item 34. The method according to any of items 24-33, the method comprising detecting (S109) based on the detected input audio signal that a face shield is worn by the second user.

Item 35. The method according to item 34, wherein the contact data comprises a face shield parameter indicating presence of the face shield.

Item 36. The method according to any of items 24-35, the method comprising detecting (S111), based on the detected input audio signal, a coughing and/or a sneezing.

Item 37. The method according to any of items 24-36, the method comprising determining (S113) an estimate of risk of exposure based on a learning model for risk of exposure and the contact data.

Item 38. The method according to item 37, the method comprising adjusting (S114) the one or more criteria based on the learning model.

Item 39. The method according to the any of items 37-38 the method comprising training (S116) the learning model based on the contact data.

Item 40. The method according to any of items 24-39, the method comprising transmitting (S118) the contact data to an external device.

Item 41. The method according to any of items 24-40, the method comprising notifying (S120) the first user based on the contact data.

Item 42. The method according to any of items 24-41, the method comprising generating (S122) a list of connection identifiers comprising a first connection identifier.

Item 43. The method according to any of items 24-42, the method comprising transmitting (S105), via the interface, to the second electronic device, a voice biometric indicative of the first user.

Item 44. The method according to any of items 24-43, wherein the activating (S106) comprises activating (S106A) the microphone circuitry to continuously detect an input audio signal.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

It may be appreciated that FIGS. 1-3B comprise some circuitries or operations which are illustrated with a solid line and some circuitries or operations which are illustrated with a dashed line. Circuitries or operations which are comprised in a solid line are circuitries or operations which are comprised in the broadest example. Circuitries or operations which are comprised in a dashed line are examples which may be comprised in, or a part of, or are further circuitries or operations which may be taken in addition to circuitries or operations of the solid line examples. It should be appreciated that these operations need not be performed in order presented. Furthermore, it should be appreciated that not all of the operations need to be performed. The example operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the examples may be implemented at least in part by means of both hardware and software, and that several "means", "units" or "devices" may be represented by the same item of hardware.

The various example methods, devices, nodes and systems described herein are described in the general context of method steps or processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program circuitries may include routines, programs, objects, components, data structures, etc. that perform specified tasks or implement specific abstract data types. Computer-executable instructions, associated data structures, and program circuitries represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed disclosure, and it will be made obvious to those skilled in the art that various changes and modifications may be made without departing from the scope of the claimed disclosure. The specification and drawings are, accordingly, to be regarded in an illustrative rather than restrictive sense. The claimed disclosure is intended to cover all alternatives, modifications, and equivalents.

What is claimed is:

1. A first electronic device, wherein the first electronic device is configured to be operated by a first user,
the first electronic device comprising:
an interface;
microphone circuitry;
memory circuitry; and
processor circuitry;
wherein the first electronic device is configured to:
discover, via the interface, a first wireless network;
receive, via the interface, directly from a second electronic device discovering the first wireless network, a voice biometric indicative of a second user;
upon the second electronic device discovering the first network and upon the first electronic device receiving the voice biometric indicative of the second user, activate the microphone circuitry to detect an input audio signal, wherein the detected input audio signal comprises an extracted voice biometric associated with the second user;
determine whether the detected input audio signal satisfies one or more criteria, the determination comprises a comparison of the detected input audio signal with the received voice biometric,
when the detected input audio signal satisfies the one or more criteria:
determine a parameter indicative of a level of risk of exposure to a disease or affliction; and
generate, based on the parameter, contact data.

2. The first electronic device according to claim 1, wherein the one or more criteria comprises a first criterion based on a first threshold and on the comparison, and wherein the first criterion is satisfied when the detected input audio signal matches the received voice biometric at least by or above the first threshold.

3. The first electronic device according to claim 1, wherein the one or more criteria comprises a second criterion based on a second threshold; wherein the second criterion is satisfied when a voice level of the detected input audio signal is above the second threshold.

4. The first electronic device according to claim 1, wherein the one or more criteria comprises a third criterion based on a third threshold; wherein the third criterion is satisfied when a duration of contact is above the third threshold.

5. The first electronic device according to claim 4, wherein the duration of contact is determined based on the detected input audio signal and a range.

6. The first electronic device according to claim 1, wherein the contact data is indicative of a first user identifier of the first user associated with a second user identifier of the second user.

7. The first electronic device according to claim 1, wherein the first electronic device is configured to detect based on the detected input audio signal that a face shield is worn by the second user.

8. The first electronic device according to claim 1, wherein the contact data comprises a face shield parameter indicating presence of the face shield.

9. The first electronic device according to claim 1, wherein the first electronic device is configured to detect, based on the detected input audio signal, a coughing and/or a sneezing.

10. The first electronic device according to claim 1, wherein the first electronic device is configured to determine an estimate of risk of exposure based on a learning model for risk of exposure and the contact data.

11. The first electronic device according to the claim 10, wherein the first electronic device is configured to adjust the one or more criteria based on the learning model.

12. The first electronic device according to claim 10, wherein the first electronic device is configured to train the learning model based on the contact data.

13. The first electronic device according to claim 1, wherein the first electronic device is configured to transmit the contact data to an external device.

14. The first electronic device according to claim 1, wherein the first electronic device is configured to notify the first user based on the contact data.

15. The first electronic device according to claim 1, wherein the first electronic device is configured to generate a list of connection identifiers comprising a first connection identifier associated with the first wireless network.

16. The first electronic device according to claim 1, wherein the first electronic device is configured to transmit, via the interface, to the second electronic device, a voice biometric indicative of the first user.

17. The first electronic device according to claim 1, wherein the first electronic device is configured to deactivate the microphone circuitry for detection of the input audio signal, when the audio input signal is determined to satisfy the one or more criteria.

18. The first electronic device according to claim 1, wherein the microphone circuitry is turned on only briefly upon the discovery of the first wireless network by the second electronic device.

19. The first electronic device according to claim 1, wherein the voice biometric indicative of the second user is encrypted with homomorphic encryption.

20. A method, performed by a first electronic device, for contact tracing, wherein the first electronic device comprises an interface; microphone circuitry; memory circuitry; and processor circuitry; the method comprising:
  discovering, via the interface, a first wireless network;
  receiving, via the interface, directly from a second electronic device discovering the first wireless network, a voice biometric indicative of a second user, wherein the second electronic device is configured to be operated by the second user;
  activating the microphone circuitry to detect an input audio signal;
  determining whether the detected input audio signal satisfies at least one of one or more criteria,
  when the detected input audio signal satisfies the at least one of the one or more criteria:
    determining a parameter indicative of a level of risk of exposure to a disease or affliction; and
    generating contact data based on the parameter.

\* \* \* \* \*